United States Patent [19]

Luly et al.

[11] Patent Number: 4,725,584

[45] Date of Patent: Feb. 16, 1988

[54] PEPTIDYL-1-AMINO-2,4-DIOLS

[75] Inventors: Jay R. Luly; Jacob J. Plattner, both of Libertyville; Hing L. Sham, Waukegan, all of Ill.

[73] Assignee: Abbott Laboratories, North Chicago, Ill.

[21] Appl. No.: 830,614

[22] Filed: Feb. 19, 1986

[51] Int. Cl.$^4$ .................. A61K 31/65; A61K 37/43; C07K 5/06; C07K 7/02; C07C 125/06; C07C 103/20

[52] U.S. Cl. .................................. 514/19; 514/18; 514/478; 560/159; 564/155; 530/332; 530/331

[58] Field of Search ..................... 514/19, 18, 478; 560/159; 564/155; 530/331, 332

[56] References Cited

U.S. PATENT DOCUMENTS 4,548,926 10/1985 Matsueda et al. ................ 514/19

OTHER PUBLICATIONS

Chem. Letter, pp. 1041–1044, (1985).

Primary Examiner—Delbert R. Phillips
Attorney, Agent, or Firm—Steven F. Weinstock; Martin L. Katz

[57] ABSTRACT

The invention relates to renin inhibiting compounds of the formula

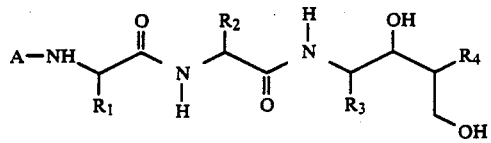

wherein A is an N-protecting group; $R_1$, $R_2$, $R_3$ and $R_5$ are independently selected from loweralkyl or lipophilic or aromatic amino acid side chains; and $R_4$ is hydrogen, loweralkyl, loweralkylmercapto or loweralkylsulfonyl.

5 Claims, No Drawings dropwise over the course of 20 minutes. After 10 minuets, the mixture was cooled to −78° C. and Boc-cyclohexylalaninal [7.92 g, 31.0 mmol, prepared by Swern oxidation (Mancuso, A. J.; Huang, S. -L.; and Swern, D. *J. Org. Chem.* 1978, 43, 2480) of Boc-cyclohexylalaninol] in dry THF (20 mL) was added over the course of 5 minutes. The mixture was warmed at ambient temperature for 45 minutes and was then quenched with saturated NH$_4$Cl (40 mL). The THF was evaporated in vacuo, and the residue was partitioned between ethyl acetate (150 mL) and water (20 mL). The organic layer was washed with saturated K$_2$CO$_3$ (45 mL) and brine (2×50 mL). Drying and evaporation provided crude material which was chromatographed on SiO$_2$ (88/12, hexane/ethyl acetate) to give 6.04 g (60%) of the desired compound.

Anal. calcd. for C$_{18}$N$_{31}$NO$_4$: C, 66.4; H, 9.6; N, 4.3. Found: C, 66.4, H, 9.4; N, 4.2. Mass spectrum: (M+H)$^+$=326.

EXAMPLE 2

4(S)-t-Butyloxycarbonylamino-5-cyclohexylpent-2(E)-enol

To a stirred 0° C. solution of the resultant compound of Example 1 (2.20 g, 6.76 mmol) in dry toluene (25 mL) was added diisobutylaluminum hydride (15.0 mL of a 1.5M solution in toluene). After 2 hours the mixture was quenched with methanol and poured into a 0° C. solution of saturated aqueous Rochelle salts (12 mL) and water (70 mL). The mixture was filtered, and the filtrate was washed (brine), dried (MgSO$_4$), filtered and evaporated to a solid. Silica gel chromatography with hexane/ethyl acetate mixtures provided 1.13 g (59%) of the desired compound.

Anal. calcd. for C$_{16}$H$_{29}$NO$_3$: C, 67.8., H, 10.3; N, 4.9. Found: C, 67.7; H, 10.1; N, 4.6. Mass spectrum: (M+H)$^+$=284.

EXAMPLE 3

4(S)-t-Butyloxycarbonylamino-5-cyclohexyl-2(R),3(R)-oxopentanol

To a stirred solution of the product of Example 2 (1.22 g, 4.30 mmol) in dichloromethane (30 mL) was added 3-chloroperoxybenzoic acid (3.52 g of 80% pure material, 15.1 mmol). After 24 hours, the mixture was diluted with ether and washed sequentially with 0° C. 1M Na$_2$SO$_3$ (3×8 mL), water (8 mL), saturated NaHCO$_3$ (3×8 mL) and brine (8 mL). Drying (Na$_2$SO$_4$), evaporation in vacuo, and chromatography (SiO$_2$, 1/1, ethyl acetate/hexane) provided 401 mg (31%) of the desired material. Mass spectrum: M$^+$=299.

Anal. calcd. for C$_{16}$H$_{29}$NO$_4$: C, 64.2; H, 9.8; N, 4.7. Found: C, 63.6; H, 9.9; N, 4.5.

EXAMPLE 4

4(S)-t-Butyloxycarbonylamino-5-cyclohexyl-3(S)-hydroxy-2(S)-isopropylpentanol

To a stirred −35° 1 C. suspension of CuI (9.5 mg, 0.05 mmol) in dry THF (5 ml) was added isopropyl magnesium bromide (0.50 ml of 2M solution in ether). A solution of the resultant compound of Example 3 (50 mg, 0.167 mmol) in THF (1.0 ml) was then added. The mixture was warmed to 0° C. over 1.25 hours at which time it was poured into saturated aqueous ammonium chloride and extracted with ether. The combined ether extracts were washed (brine.), dried (Na$_2$SO$_4$), filtered and evaporated. The residue (70 mg) was chromatographed on silica gel eluting with ether/hexane mixtures to give 23 mg (40%) of the desired compound. Mass spectrum: M$^+$=343.

EXAMPLE 5

4(S)-t-Butyloxycarbonylamino-5-cyclohexyl-3(S)-hydroxy-2(S)-isopropylmercaptopentanol To a 40° C. solution of the resultant compound of Example 3 (100 mg, 0.334 mmol) and triethylamine (40 mg, 0.40 mmol) in methanol (3.3 ml) was added isopropyl mercaptan (76 mg, 1 mmol). The solvent was evaporated after 24 hours, and the residue was chromatographed in silica gel to give 81 mg (65%) of the desired compound.

EXAMPLE 6

Methyl 4(S)-t-Butyloxycarbonylamino-5-cyclohexylpent-2(Z)-enoate

The aldehyde generated by the procedure of Example 1 was treated under conditions of a modified Horner-Emmons olefination (Still, W. C.; Gennari, C. *Tetrahedron Lett.*, 1983, 24, 4405) to give the desired product in 62% yield after word up and chromatography.

EXAMPLE 7

4(S)-t-Butyloxycarbonylamino-5-cyclohexylpentyl-2-(Z)-enol

Following the procedure of Example 2, but replacing the resultant compound of Example 1 with the resultant compound of Example 6, gave the desired material.

EXAMPLE 8

4(S)-t-Butyloxycarbonylamino-5-cyclohexyl-2(S),3(R)-oxopentanol

Following the procedure of Example 3, but replacing the resultant compound of Example 2 with the resultant compound of Example 7, gave the desired compound.

EXAMPLE 9

4(S)-t-Butyloxycarbonylamino-5-cyclohexyl-3(S)-hydroxy-2(R)-isopropylmercaptopentanol Following the procedure of Example 5, but replacing the resultant compound of Example 3 with the resultant compound of Example 8, gave the desired material.

EXAMPLE 10

Boc-Phe-His Amide of 4(S)-Amino-5-cyclohexyl-3(S)-hydroxy-2(S)-isopropylpentanol The resultant compound of Example 4 (15 mg, 0.044 mmol) was treated with 2.2M HCl in anhydrous methanol (4 ml) for 6 hours. Evaporation gave the corresponding amine hydrochloride which was dissolved in dry dimethylformamide (4 ml) along with Boc-Phe-His (17.7 mg, 0.044 mmol), 1-hydroxybenzotriazole hydrate (8.9 mg, 0.066 mmol), and N-methylmorpholine (4.4 mg, 0.044 mmol). The mixture was cooled to −23° C., and 1,3-dicyclohexylcarbodiimide (DCC, 9.1 mg, 0.044 mmol) was added. The mixture was allowed to warm to room temperature over the course of 2 hours. After stirring for an additional 18 hours, the mixture was partitioned between ethyl acetate (10 ml) and water (5 ml). The organic layer was washed sequentially with saturated NaHCO$_3$ (2×4 ml) and brine (4 ml). Drying,

PEPTIDYL-1-AMINO-2,4-DIOLS

TECHNICAL FIELD

This is a continuation-in-part of U.S. patent application, Ser. No. 693,951, filed Jan. 23, 1985 abandoned.

The present invention relates to novel organic compounds which inhibit renin, processes for making such compound, synthetic intermediates employed in these processes and method of treating hypertension with such compounds.

BACKGROUND ART

Renin is a proteolytic enzyme synthesized and stored principally in a specific part of the kidney called the juxtaglomerular apparatus. Any of three different physiologic circumstances may cause the release of renin into the circulation: (a) a decrease in the blood pressure entering or within the kidney itself; (b) a decrease in the blood volume in the body; or (c) a fall in the concentration of sodium in the distal tubules of the kidney.

When renin is released into the blood from the kidney, the renin-angiotensin system is activated, leading to vasoconstriction and conservation of sodium, both of which result in increased blood pressure. The renin acts on a circulating protein, angiotensinogen, to cleave out a fragment called angiotensin I (AI). AI itself has only slight pharmacologic activity but, after additional cleavage by a second enzyme, angiotensin converting enzyme (ACE), forms the potent molecule angiotensin II (AII). The major pharmacological effects of AII are vasoconstriction and stimulation of the adrenal cortex to release aldosterone, a hormone which causes sodium retention. AII is cleaved by an aminopeptidase to form angiotensin III (AIII), which, compared to AII, is a less potent vasoconstrictor but a more potent inducer of aldosterone release.

Inhibitors of renin have been sought as agents for control of hypertension and as diagnostic agents for identification of cases of hypertension due to renin excess.

With these objectives in mind, the renin-angiotension system has been modulated or manipulated, in the past, with ACE inhibitors. However, ACE acts on several substrates other than angiotensin I (AI), most notably the kinins which cause such undesirable side effects as pain, "leaky" capillaries, prostaglandin release and a variety of behavioral and neurologic effects. Further, ACE inhibition leads to the accumulation of AI. Although AI has much less vasoconstrictor activity than AII, its presence may negate some of the hypotensive effects of the blockade of AII synthesis.

Inhibition of other targets in the renin-angiotensin system such as AII with compounds such as saralasin can block AII activity, but would leave unimpaired and perhaps enhance the hypertensive effects of AIII.

On the other hand, there are no known side effects whih result when renin is inhibited from acting on its substrate. Considerable research efforts have thus been carried out to develop useful inhibitors of renin. Past research efforts have been directed to renin antibodies, pepstatin, phospholipids and substrate analogs such as tetrapeptides and octapeptides to tridecapeptides. These inhibitors either demonstrate poor activity in inhibiting renin production or poor specificity for inhibiting renin only. However, Boger et al. have reported that statine-containing peptides possess potent and specific renin-inhibiting activity (*Nature*, Vol. 303, p. 81, 1983). In addition, Szelke and co-workers have described polypeptide analogs containing a non-peptide link (*Nature*, Vol. 299, p. 555, 1982) which also cause potent renin inhibition and show a high specificity for this enzyme.

DISCLOSURE OF THE INVENTION

The invention relates to renin inhibiting compounds of the formula

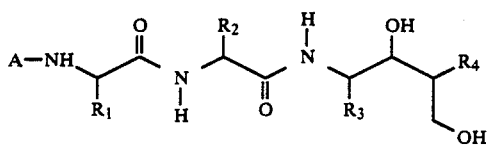

wherein A is an N-protecting group; $R_1$, $R_2$, $R_3$ and $R_5$ are independently selected from loweralkyl or lipophilic or aromatic amino acid side chains; and $R_4$ is hydrogen, loweralkyl, lowralkylmercapto or loweralkylsulfonyl.

The chiral centers of the compounds of the invention may have either the "R" or "S" configuration but preferably have an "S" configuration except where noted.

The term "N-protecting group" as used herein refers to those groups intended to protect the N-terminus against undesirable reactions during synthetic procedures or to prevent the attack of exopeptidases on the final compounds or to increase the solubility of the final compounds and includes but is not limited to acyl, acetyl, pivaloyl, t-butylacetyl, t-butyloxycarbonyl(Boc), carbobenzyloxycarbonyl or benzoyl groups or an L- or D- aminoacyl residue, which may itself be N-protected similarly.

The term "loweralkyl" as used herein refers to straight or branched chain alkyl radicals containing from 1 to 6 carbon atoms including but not limited to methyl, ethyl, n-propyl, iso-propyl, n-butyl, iso-butyl, sec-butyl, 2-methylhexyl, n-pentyl, 1-methylbutyl, 2,2-dimethylbutyl, 2-methylpentyl, 2,2-dimethylpropyl, n-hexyl and the like.

The term "lipophilic or aromatic amino acid side chains" as used herein refers to those amio acid side chains which have an affinity for lipids or have an aromatic ring and include but are not limited to isobutyl, isopropyl, sec-butyl, benzyl, (imidazole-4-yl)methyl, p-hydroxybenzyl, 1- and 2-naphthylmethyl, and cyclohexylmethyl. General reference to amino acid side chains in both the description and claims herein is to be taken as reference to such, whether naturally occurring in proteins or not, and to both D- and L-forms.

The terms "Ala", "His", "Leu" and "Phe" as used herein refer to alanine, histidine, leucine and phenylalanine, respectively.

The following Examples will serve to further illustrate preparation of the noval compounds of the invention.

EXAMPLE 1

Ethyl 4(S)-t-Butyloxycarbonylamino-5-cyclohexylpent-2(E)-enoate

NaH (1.86 g of a 60% dispersion in oil) was washed 3 times with hexane under a $N_2$ atmosphere and then suspended in anhydrous tetrahydrofuran (THF, 150 ml). The suspension was cooled to 0° C., and triethylphosphonoacetate (10.44 g, 46.58 mmol) was added evaporation in vacuo, and chromatography on SiO$_2$ (9/1, CH$_2$Cl$_2$/CH$_3$OH) provided 29.5 mg (47%) of the desired compound.

EXAMPLE 11

Boc-Phe-His Amide of 4(S)-Amino-5-cyclohexyl-3(S)-hydroxy-2(S)-isopropylmercaptopentanol Following the procedure of Example 10, but replacing the resultant compound of Example 4 with the resultant compound of Example 5, gave the desired product.

EXAMPLE 12

Boc-Phe-His Amide of 4(S)-Amino-5-cyclohexyl-3(S)-hydroxy-2(R)-isopropylmercaptopentanol Following the procedure of Example 10, but replacing the resultant compound of Example 4 with the resultant compound of Example 9, gave the desired product.

EXAMPLE 13

Boc-Phe-His Amide of 4(S)-Amino-5-cyclohexyl-3(S)-hydroxyl-2(S)-(isopropylsulfonyl)pentanol The resultant compound of Example 11 was treated with 2 equivalents of 3-chloroperoxybenzoic acid in dichloromethane to give the desired product after chromatography.

EXAMPLE 14

4-t-Butyloxycarbonylamino-3-hydroxy-6-methylhept-1-ene

To a stirred 0° C. solution of Boc-leucinal (3.00 g, 13.9 mmol) in dry THF (70 ml) was added vinyl magnesium bromide (35 ml of a 1.0M solution in THF). After 5 hours, the mixture was quenched with 1.0M NH$_4$Cl (50 ml). Most of the THF was evaporated in vacuo and the residue was extracted with ether several times. The combined extracts were washed (brine), dried (Na$_2$SO$_4$), filtered, and evaporated to give the desired product as a 3:2 mixture of hydroxydiastereomers in 65% field.

EXAMPLE 15

Boc-Phe-Ala Amide of 4-Amino-3-hydroxy-6-methyl-1-heptene

The resultant compound of Example 14 (1.00 g, 4.11 mmol) was treated with 1M HCl in anhydrous methanol (80 ml) for 15 h. Evaporation gave the corresponding amine hydrochloride which was used below without further purification.

To a stirred −12° C. solution of Boc-Phe-Ala-OH in dry THF (30 ml) was added N-methylmorpholine (NMM, 338 mg) followed by isobutylchloroformate (456 mg). After 3 minutes, a −12° C. solution of the above salt and NMM (338 mg) in dry THF (10 ml) was added dropwise over the course of 5 minutes. After warming to room temperature for 2 hours, the solvent was evaporated, and the residue was partitioned between ethyl acetate (200 ml) and saturated NaHCO$_3$ (10 ml). The organic phase was washed with saturated NaHCO$_3$ (10 ml), and the combined aqueous washes were back extracted with ethyl acetate (10 ml). The combined organic phase was washed with 0.1M H$_3$PO$_4$ (10 ml) and brine (10 ml). Evaporation provided 1.41 g (92%) of the desired product. Mass spectrum: M$^+$=461.

EXAMPLE 16

Boc-Phe-Ala Amide of 4-Amino-1,3-dihydroxy-6-methylheptane

To a stirred solution of the resultant product of Example 15 (200 mg, 0.433 mmol) in dry THF (10 ml) was added 9-BBN (5.2 ml of a 0.5M solution in THF). After 18 hours the sequential addition of water (3 ml), 3N NaOH (0.87 ml), and, 2 minutes later, 30% H$_2$O (1.0 ml) was performed. The miture was heated to 50° C. for 1 hour, cooled to room temperature, and partitioned between ether (20 ml) and water (5 ml). The organic phase was washed (5 ml brine), dried (NaSO$_4$), concentrated, and chromatographed (40 g of 40 m SiO$_2$; 95:5, CH$_2$Cl$_2$:CH$_3$OH) to give 126 mg (61%) of the desired product. Mass spectrum: M$^+$=479.

The compounds of the present invention can be used in the form of salts derived from inorganic or organic acids. These salts include but are not limited to the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptonate, hexanoate, hydrochloride, hydrobromide, hydroiodide, 2-hydroxy-ethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl., and diamyl sulfates, long chain halides such as decyl, lauryl, myristyl, and stearyl chlorides, bromides and iodides, aralkyl halides like benzyl and phenethyl bromides, and others. Water or oil-soluble or dispersible products are thereby obtained.

The novel compounds of the present invention possess an excellent degree of activity and specificity in treating renin-associated hypertension in a host. The ability of the compounds of the invention to inhibit human renal renin can be demonstrated in vitro by reacting a selected compound at varied concentrations with human renal renin, free from acid proteolytic activity, and with human renin substrate (angiotensinogen) at 37° C. and pH 6.0. At the end of the incubation, the amount of angiotensin I formed is measured by radioimmunoassay and the molar concentration required to cause 50% inhibition, expressed as the IC$_{50}$, is calculated. When tested in accordance with the foregoing procedure, the compounds of the invention demonstrated IC$_{50}$'s in the range of $10^{-5}$ to $10^{-10}$M.

Total daily dose administered to a host in single or divided doses may be in amounts, for example, from 0.001 to 10 mg/kg body weight daily and more usually 0.01 to 1 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level of any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, by inhalation spray, rectally, or topically in dosage unit formulations containing conventional nontoxic pharmaceutically acceptable carriers, adjuvants, and vehicles as desired. The term parenteral as used herein includes subcutaneous injections, intravenous, intramuscular, intrasternal injection, or infusion techniques.

Injectable preparation, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer s solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The foregoing is merely illustrative of the illustrative and is not intended to limit the invention to the disclosed compounds. Variations and changes which are obvious to one skilled in the art are intended to be within the scope and nature of the invention which are defined in the appended claims.

What is claimed is:

1. A renin inhibiting compound of the formula:

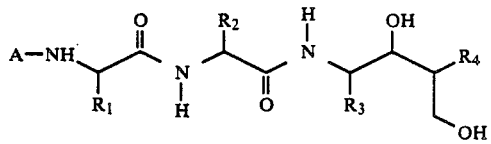

wherein A is an N-protecting group; $R_1$ is (aryl)methyl; $R_2$ is selected from loweralkyl and imidazoylmethyl; $R_3$ is cycloalkylalkyl; and $R_4$ is loweralkyl, loweralkylmercapto or loweralkylsulfonyl.

2. The renin inhibiting compound of claim 1 wherein $R_1$ is benzyl; $R_2$ is (4-imidazoyl)methyl; and $R_3$ is cyclohexylmethyl.

3. The renin inhibiting compound of claim 2 wherein A is Boc and $R_4$ is isopropylmercapto.

4. A pharmaceutical composition for treating renin-associated hypertension, comprising a pharmaceutical carrier and a therapeutically effective amount of the compound of claim 1.

5. A method of treating hypertension comprising administering to a host in need of such treatment a therapeutically effective amount of a compound of claim 1.

* * * * *